United States Patent [19]

Illig

[11] Patent Number: 5,342,605

[45] Date of Patent: Aug. 30, 1994

[54] POLYMERIC X-RAY COMPOSITIONS CONTAINING IODINATED POLYMERIC BEADS

[75] Inventor: Carl R. Illig, Phoenixville, Pa.

[73] Assignee: Sterling Winthrop Inc., Malvern, Pa.

[21] Appl. No.: 54,119

[22] Filed: Apr. 26, 1993

Related U.S. Application Data

[63] Continuation-in-part of Ser. No. 877,690, May 1, 1992, abandoned.

[51] Int. Cl.$^5$ .................. A61K 49/04; A61K 31/715; A61K 31/075
[52] U.S. Cl. .......................................... 424/5; 514/54; 514/57; 514/717; 514/941; 514/942
[58] Field of Search ................... 424/5, 4; 514/54, 57, 514/717, 941, 942; 568/580, 656

[56] References Cited

U.S. PATENT DOCUMENTS

| | | | |
|---|---|---|---|
| 2,832,722 | 8/1958 | Singher | 167/95 |
| 4,069,306 | 1/1978 | Rothman | 424/4 |
| 4,120,946 | 10/1978 | Quemille et al. | 424/4 |
| 4,744,975 | 5/1988 | Suami et al. | 424/5 |
| 5,019,370 | 5/1991 | Jay et al. | 424/4 |
| 5,141,739 | 8/1992 | Jung et al. | 424/4 |
| 5,186,922 | 2/1993 | Shell et al. | 128/654 |

*Primary Examiner*—Gary E. Hollinden
*Attorney, Agent, or Firm*—Arthur Rosenstein; Imre (Jim) Balogh

[57] ABSTRACT

Disclosed are x-ray contrast compositions for oral or retrograde examination of the gastrointestinal tract comprising a polymeric material in combination with a divalent cation capable of forming a coating on the gastrointestinal tract and iodinated polymeric, water-insoluble beads having a particle size of from about 0.01 to about 1000μ wherein said iodinated polymeric beads comprise a polymer containing repeating units of the formula (I)

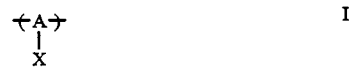

wherein
A is a repeating organic unit in the backbone chain of the polymer; and
X is an organic moiety containing or iodinated eromatic group and a hydrophilic group, said moiety having an iodine content within the range of from about 40 to about 80 weight percent based or the molecular weight of X, in a pharmaceutically acceptable carrier.

1 Claim, No Drawings

POLYMERIC X-RAY COMPOSITIONS CONTAINING IODINATED POLYMERIC BEADS

CROSS REFERENCE TO RELATED APPLICATION

This is a continuation-in-part of application Ser. No. 07/877,690 filed on May 1, 1992, now abandoned.

BACKGROUND OF THE INVENTION

1. Field of the Invention

This invention relates to an X-ray contrast composition for oral or retrograde administration to a mammal comprising water-insoluble iodinated polymeric beads as the contrast producing agent and a film-forming material.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and nonirritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. The drawbacks of unevenly coating of the mucosa with an insufficiently adherence thereto proved to be rather difficult to solve. To that end, the use of certain polymer additives were proposed as illustrated hereunder.

U.S. Pat. No. 4,069,306 discloses an X-ray contrast preparation which is said to adhere to the walls of body cavities. The preparation comprises a finely divided water-insoluble inorganic X-ray contrast agent and minute particles of a hydrophilic polymer which is insoluble in water but is water-swellable. The body cavity is supplied with such preparation suspended in water. The X-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to X-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved X-ray imaging medium that uniformly coats the soft tissues subjected to diagnostic X-ray examination.

In U.S. patent application Ser. No. 07/938,786, it was disclosed that the uniform coating of the mucosa of the intestine can be obtained by barium sulfate in combination with a film-forming material to provide high quality x-ray results.

It has now been discovered that high quality X-ray results can be obtained by utilizing a formulation comprising water-insoluble iodinated polymeric beads in combination with a film-forming material.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an X-ray emitting device, a polymeric film former, which has incorporated therein water-insoluble iodinated polymeric beads, capable of coating the GI tract. Upon completion of the GI imaging examination, the removal of the coating occurs as a result of the normal turnover of cells, that is, within about 24 to 48 hours. Such compositions must meet several requirements: the film former must be nontoxic; must not contain leachable or digestible components that would deleteriously affect the patient; and the composition must be capable of forming a film in the pH range of from about 5 to about 8.

The object of the present invention is achieved by a composition comprising: water-insoluble iodinated polymeric beads; polymeric material which is at least partially water soluble and contains polarizable or ionizable groups; and a divalent metal ion selected from the group consisting of Mg++, Ca++, Zn++ and Ba++ which potentiates the effect of the polymeric material as a film former on the mucosa of the GI tract.

The water-insoluble iodinated polymeric beads, the polymeric film former and the divalent metal ion are incorporated in a solid or liquid media for administration to a mammal for X-ray visualization of the GI tract.

The iodinated polymeric beads are water-insoluble, non-water swellable in finely-divided form having a particle size of from about 0.01 to about 1000µ. The iodinated polymer from which the beads are produced by comminution or other techniques known in the art, has an iodine content in excess of 35 weight percent based on the day weight of the polymer and contains repeating units of the formula:

wherein
A is a repeating organic unit in the backbone chain of the polymer, and
X is an organic moiety containing an iodinated aromatic group and a hydrophilic group, said moiety having an iodine content within the range of from about 40 to 80 weight percent based on the molecular weight of X.

A preferred embodiment of the invention features a crosslinked, iodinated polymer of formula I wherein A represents the residue of a repeating unit in the backbone chain of a polymer having appended hydroxyl groups, the hydroxyl groups providing crosslinking sites and reaction sites for attachment of the moiety X.

The iodinated polymeric beads, the polymeric film former and the divalent metal ion are incorporated in a solid or liquid media for administration to a mammal for X-ray visualization of the GI tract.

DETAILED DESCRIPTION OF THE INVENTION

Starting materials, reagents and solvents can be obtained from chemical suppliers, such as Aldrich, Baker, DuPont and Eastman Chemical Companies, or they may be prepared by techniques known in the prior art.

The polymers that were found to be suitable for forming a thin coating on the GI tract can be classified as anionic, cationic and neutral polymers, a description of which follows. U.S. Pat. No. 4,623,539, the disclosure of which is incorporated herein by reference, pertains to such polymers.

The water-insoluble iodinated polymeric beads utilized in the present invention are disclosed in U.S. Pat. No. 4,406,878, the disclosure of which is incorporated herein by reference.

The general structural formula of iodinated polymers of the invention is represented by structural formula I above. The backbone chain of the iodinated polymer can represent:
(i) a condensation polymer such as a polyester, polyamide, polyurethane, polycarbonate, polyepoxide, polyether, a phenolformaldehyde polymer and equivalent condensation polymers;
(ii) an addition polymer produced by the polymerization of one or more addition polymerizable monomers containing a polymerizable unsaturated double bond, e.g., vinyl monomers, including such addition polymers as poly(vinyl alcohol), poly(alkylmethacrylates), poly(alkylacrylates), and equivalent addition polymers; or
(iii) a naturally occurring polymer, for example, a polysaccharide containing repeating glucose units such as starch, glycogen, cellulose, cellulosic derivatives, and equivalent naturally occuring polymers.

Preferably, repeating units A of formula I represents the residue of a repeating unit having an appended hydroxyl group, such as the repeating unit of poly (vinyl alcohol), the repeating epoxy unit of a polyepoxide, the repeating unit of a hydroxylated acrylic polymer such as poly (hydroxyethylacylate), or the repeating glucose unit of a naturally occurring polysaccharide. The appended hydroxyl group can serve either as a crosslinking site or as a reaction site for precursor compounds of the organic moiety X in formula I. Such precursor compounds can be chemically linked to the repeating units of the polymer backbone chain through a condensation reaction with the appended hydroxy group.

The organic moiety X of formula I above represents an iodine-containing organic fragment comprising an iodinated aromatic group and one or more hydrophilic groups. To obtain the high iodine content characteristic of the polymers used in the invention, the iodinated aromatic group have multiple iodine substituents bonded directly to the aromatic carbon ring atoms. Especially preferred among these iodinated aromatic groups are aromatic groups containing three, preferably four, carbon ring atoms substituted by iodine. A preferred iodinated aromatic group is an iodinated phenyl ring, although napthyl rings and nitrogen-containing heterocyclic rings containing 5 to 7 ring atoms can also be used. An especially preferred iodinated aromatic group is a phenyl ring bearing iodine substituents on a 4 of the carbon ring atoms.

The hydrophilic group(s) of X are typically present as a substituent(s) bonded directly, or indirectly through a chemical linking group, to one or more of the carbon ring atoms of the iodinated aromatic group. Preferred linking groups include short chain aliphatic groups, e.g., alkylene groups, amido groups and equivalent aliphatic groups, having 1 to 4 carbon atoms. Typically hydrophilic groups can be selected from a variety of such groups including carboxyl groups; sulfo groups; amino groups; salts thereof such as carboxylate salts, sulfonate salts, ammonium salts; polyols such as glucose groups; and equivalent hydrophilic groups.

Typically, the precursors from which the organic moiety X of formula I is derived contains a reactive group which forms a chemical linking group with the repeating unit of the polymer backbone chain. In the preferred embodiment of the invention wherein the repeating unit of the polymer backbone chain represents the residue of a repeating unit bearing a hydroxyl group, the reactive group contained on the precursor of X is a group reactive with the hydroxy group. For example, the reactive group can be a carboxyl group which condenses with the appended hydroxy group of the backbone chain to form an ester group linking an iodinated aromatic moiety of the polymer backbone. A variety of other reactive groups which react with a hydroxy group to form such chemical linking groups as ethers, amides, thioesters, carbonates, carbamates, sulfides, and equivalents, can also be used.

A partial listing of precursors for the moiety X of formula I includes, for example, 3-(3-amino-2,4,6-triiodophenyl)-2-ethylpropionic acid; 3-(3-hydroxy-2,4,6-triiodophenyl)-2-ethylpropionic acid; sodium 3-(3-butyrylamino-2,4,6-triiodophenyl)- 2-ethylacrylate; 3,5-diiodo-4-pyridone-N-acetic acid; 3-acetamido-2,4,6-triiodobenzoic acid; tetraiodophthalic anhydride; and the like. Tetraiodophthalic anhydride can be particularly useful because of its high iodine content.

Based on the foregoing description, a structural formula of certain preferred iodinated polymers can be illustrated as

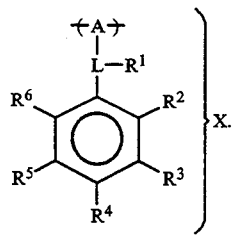

wherein:

A is as defined in formula I above;

X is as defined in formula I above;

L represents one of the above-described linking groups, e.g. ester, ether, amide, thioester, carbonate, carbamate, sulfide and the like; and each of $R_1$ to $R_6$ which may be the same or different, represents hydrogen, an iodine-containing substituent, or a hydrophilic group-containing substituent, with the proviso that the iodine content of X is from about 40 to 80 percent (based on the molecular weight of X).

Preferred iodinated polymers are crosslinked. This can enhance the water-insolubility and resistance to swell properties of the polymer. Crosslinking can be effected by incorporation of suitable crosslinking sites either on the polymer backbone chain or on the moiety X or both. For example, in a preferred embodiment wherein the polymer contains a repeating backbone unit bearing an appended hydroxyl group and a sidechain group A containing a carboxyl group as a hydrophilic group, a hydroxyl group appended to the backbone chain of one polymer can react with the carboxyl group attached to the sidechain X of another polymer, thereby crosslinking the two polymers through an ester linkage.

The polymeric contrast agents of the invention contain both hydrophilic and hydrophobic groups. Repeating backbone units A of formula I are substantially hydrophobic as are many portions of the moiety X. Of course X also contains one or more hydrophilic groups. This combination of hydrophobic and hydrophilic groups is believed important to provide the proper polymer surface and electrical characteristics which, in turn, provide proper polymer compatibility with body organs and tissues.

The iodinated polymers can be prepared by any of a variety of conventional polymerization and chemical reaction techniques. A preferred reaction sequence is to chemically react precursor compounds for the sidechain group X with a preformed polymer containing appended groups serving as suitable reaction sites, e.g., hydroxyl groups. The preformed polymer can be prepared by addition or condensation polymerization, depending on the polymer; or it can be obtained from naturally occurring sources in the case of naturally occurring polymers; e.g., polysaccharides. The precursor compounds for the moiety X can be reacted with the reaction site on the polymer backbone by a variety of wellknown reaction procedures, depending on the nature of the linking group L in formula II above which is formed in this reaction. Advantageously, the reaction of these precursor compounds is carried out under emulsifying conditions so that the resultant polymers are obtained in finely-divided particulate form. Crosslinking can be carried out during or following attachment of the moiety X of the polymer backbone.

EXAMPLE 1

Five and one-half grams of poly (vinyl alcohol), PVA, purchased under the trademark Elvanol 52-22 from DuPont was swelled with stirring overnight in 300 ml of pyridine. The mixture was stirred for 4 days at room temperature with 65 g of tetraiodophthalic anhydride to react the PVA with the anhydride. The mixture was then heated to 60° C. for 8 hours to effect crosslinking. A copious precipitate of the iodinated polymeric reaction product formed. This was filtered off and washed with water and dried. Analysis showed that the polymeric reaction product has an iodine content of 61.7 percent compared with a theoretical value of 73.0 percent for complete reaction. The structure of a repeating unit of this iodinated polymeric reaction product was as follows:

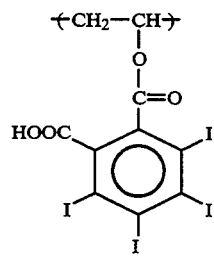

Having obtained a water-insoluble and non-water-swellable iodinated polymer as described above, the polymer can be subjected to grinding or milling treatment to obtain polymer particles of the appropriate size range. Of course, in cases where the polymers are prepared under suitable conditions, such as bead polymerization or emulsifying conditions, the polymers may already have an appropriate particle size so that additional milling or grinding may be unnecessary. A useful particle size for these polymer particles is within the range of from about 0.01 to 1000 microns, preferably 0.1 to 100 microns.

The iodinated polymeric beads, the polymeric material and divalent cation are blended together and then formulated for administration using physiologically acceptable carriers or excipients in a manner within the skill of the art. The iodinated polymeric beads, with the addition of pharmaceutically acceptable aids (such as surfactants and emulsifiers) and excipients may be suspended in an aqueous medium resulting in a dispersion, suspension or emulsion. Alternatively, the iodinated polymeric beads, the polymeric material and divalent cation may be formulated into a solid form, such as tablets or capsules.

Solid compositions of the present invention shall contain, instead of surfactants/emulsifiers and water used in the liquid compositions, bulking agents and other pharmaceutically acceptable ingredients advantageously employed to render the compositions palatable.

When the x-ray composition is formulated as a tablet, the bulking agent should have good compression characteristics. Suitable bulking agents are well known in the art and include a sweetener such as sugars, e.g. sucrose, and polyhydric alcohols, e.g. mannitol, sorbitol and xylitol, and mixtures thereof. When formulated as a tablet, it is preferable to incorporate in the composition one or more tablet lubricating agents, such as stearic acid, magnesium stearate and talc. The amount of the tablet lubricating agent as well as any other ingredients required to easily prepare the solid compositions, can readily be determined by the skilled formulator. The solid compositions may have incorporated therein optional pharmaceutically acceptable ingredients in order to impart thereto additional desirable properties, such as flavorants and colorants.

Compositions

Compositions of the present invention comprise the following pharmaceutically acceptable components based on % w/v:

| Polymeric Material | 0.001–25 |
| --- | --- |
| Divalent Cation | 0.001–20 |
| Iodinated Polymeric Beads | 5–95 |
| Excipient | 0–20 |
| Aids (Surfactants/Emulsifiers) | 0.01–20 |
| Water | q.s. to 100 |

Solid compositions of the present invention comprise the following pharmaceutically acceptable components based on % w/w:

| Polymeric Material | 0.001–25 |
| --- | --- |
| Divalent Cation | 0.001–20 |
| Iodinated Polymeric Beads | 5–95 |
| Bulking Agent/Lubricant/Flavor | q.s. to 100 |

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxy-benzoate, benzoic acid or sorbic acid may also be desirable in some formulations.

Surfactants or emulsifiers can be used alone or in combination with other emulsifying agents and surfactants. For example, Dow Corning Medical Antifoam AF, which is a composition of 30% w/v polydimethylsiloxane and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The amount of such surfactants may be in the range of from 0.01 to 5% w/v of the aqueous formulations, although the amount, in general, is kept as low as possible, preferably in the range of 0.05 to 2% w/v. The surface active agents may be cationic, anionic, nonionic, zwitterionic or a mixture of two or more of these agents.

Suitable cationic surfactants include cetyltrimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the primary amide, monoethylamide and diethylamide of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:
(a) Sorbitan esters (sold under the trade name Span) having the formula:

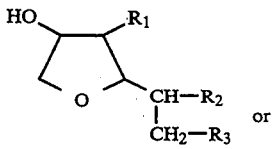

wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=$
  $(C_{11}H_{23})COO$ for laurate,
  $(C_{17}H_{33})COO$ for oleate,
  $(C_{15}H_{31})COO$ for palmirate,
  $(C_{17}H_{35})COO$ for stearate;
(b) Polyoxyethylene alkyl ethers (i.e. Brijs) having the formula:

$CH_3(CH_2)_x(O-CH_2-CH_2)_yOH$ where $(x+1)$ is the number of carbon atoms in the alkyl chain, typically:

| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60;
(c) Polyoxyethylene sorbitan fatty acid esters, sold under the trade names of Polysorbates 20, 40, 60, 65, 80 & 85; and
(d) Polyoxyethylene stearates, such as:
  poly(oxy-1,2-ethanediyl)-a-hydro-w-hydroxy-octadecanoate;
  polyethylene glycol monostearate; and
  poly(oxy-1,2-ethanediyl)-a-(1-oxooctadecyl)-w-hydroxy-polyethylene glycol monostearate.

The film former polymeric materials used in accordance with the present invention include anionic polymers, cationic polymers and neutral polymers.

I. Anionic Polymers

The anionic polymers carry negative charges in the ionized form and are capable of binding to cell surfaces mainly by electrostatic forces. Suitable anionic polymers include the following:

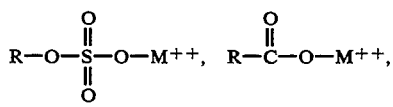

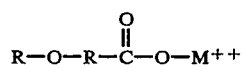

wherein
R is the polymeric chain;

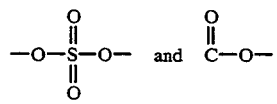

$M^{++}$ is a divalent cation.

Specific anionic polymers useful in the practice of the present invention include:
(1) Sulfated polysaccharides of the formula:

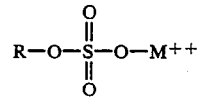

wherein R is 3,6-anhydro-D-galactose linked

| through C-4 to D-galactose; | (kappa carrageenan) |
| a-D-galactose units (1-3) linked; D-galactose | (lambda carrageenan) |
| 3,6-anhydro-D-galactose; D-galactose | (iota carrageenan) |
| 3,6-anhydro-L-galactose: D-galactose | (Agar - Agar) |
| 3,6-anhydro-D-galactose; D-glucopyranose; Galactan; and Galactosamino-glucuronans and | (Furcellaren) (Laminarin sulfate) (Galactan sulfate) (Chondroitin sulfates); |

$M++$ is $Mg++$, $Ca++$, $Zn++$, $Ba++$ or mixtures thereof.

(2) Carboxylated polysaccharides of the formula:

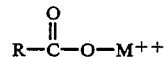

| wherein R is D-galacturonoglycan; and | (Pectin) |
| anhydro-D-mannuronic acid and anhydro-L-guluronic acid residues; and | (Algin) |

$M^{++}$ is $Mg^{++}$, $Ca^{++}$, $Zn^{++}$, $Ba^{++}$ or mixtures thereof.

(3) Cellulose derivatives of the formulae:

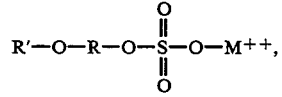

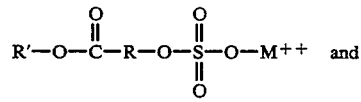

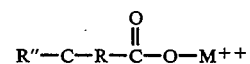

wherein
R is an anhydroglucose residue;
R' is $CH_3$, $C_2H_5$ or $C_3H_7$;
R" is $CH_3$ or $C_2H_5$; and
$M++$ is $Mg++$, $Ca++$, $Zn++$, $Ba++$ or mixtures thereof.

Examples of cellulose derivatives include: sodium ethylcellulose sulfate, sodium cellulose acetate sulfate and sodium carboxymethyl cellulose.

(4) Sulfated, sulfonated or carboxylated synthetic polymers of the formula:

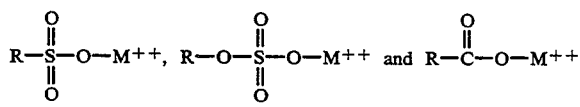

wherein
R is an aliphatic or aromatic hydrocarbon, such as polystyrene, poly(sulfon) resin or carboxylated (poly) vinyl; and
$M^{++}$ is $Mg^{++}$, $Ca^{++}$, $Zn^{++}$, $Ba^{++}$ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:
(a) Polysaccharides, such as starch, glycogen, glucan, fructans, mannans, galactomannas, glucomannas, galactans, xylans, glycuranans, dextran and starch amylose;
(b) Cellulose derivatives, such as methylcellulose, hydroxyethylcellulose, ethylhydroxyethyl cellulose, hydroxypropyl methylcellulose and hydroxypropyl cellulose; and
(c) Synthetic polymers, such as polyvinylpyrrolidone, polyvinyl alcohol and ethylene oxide polymers.

Exemplary formulations of the present invention are as shown:

Example 2

| | |
|---|---|
| Iodinated Polymeric Beads | 1.94 g (19.4% w/v) |
| Dow Corning Med. Antifoam AF emulsion | 1.50 g (15% w/v) |
| Tween 80 | 0.35 g (3.5% w/v) |
| Galactan Sulfate | 0.3 g (3% w/v) |
| Calcium Lactate | 0.3 g (3% w/v) |
| Purified Water | q.s. to 10 ml |

Example 3

| | |
|---|---|
| Iodinated Polymeric Beads | 1.50 g (15.0% w/v) |
| Tetronic 908 | 0.45 g (4.5% w/v) |
| Sodium Carrageenan solution | 2.50 g of 2% (w/v) |
| Calcium Lactate | 0.3 g (3% w/v) |
| Purified Water | q.s. to 10 ml |

Example 4

| | |
|---|---|
| Iodinated Polymeric Beads | 2.00 g (20.0% w/v) |
| Mineral Oil | 0.50 g (5% w/v) |
| Heparin | 0.25 g (2.5% w/v) |
| Tween 21 | 0.25 g (2.5% w/v) |
| Pluronic F-68 | 0.25 g (2.5% w/v) |
| Calcium Lactate | 0.25 g (2.5% w/v) |
| Purified Water | q.s. to 10 ml |

Example 5

| | |
|---|---|
| Iodinated Polymeric Beads | 1.80 g (18.0% w/v) |
| Safflower Oil | 0.50 g (5% w/v) |
| Magnesium Citrate | 0.50 g (5% w/v) |
| Span 80 | 0.4 g (4% w/v) |
| Hydroxypropyl methylcellulose (4000 cPs) | 2.50 g of 2% (w/v) solution |
| Purified Water | q.s. to 10 ml |

The compositions of the invention may be administered orally to the patient for radiological examination of the GI tract. The compositions of the invention may also be administered rectally in the form of enemas to a patient for radiologic examination of the colon.

The dosages of the contrast agent used according to the method of the present invention will vary according to the precise nature of the ingredients used. Preferably, however, the dosage should be kept as low as is consistent with achieving contrast enhanced imaging. By employing as small amount of the composition as possible, toxicity potential is minimized. For most formulations of the present invention dosages will be in the range of from about 0.1 to about 20.0 g I/kg body weight, preferably in the range of from about 0.4 to about 8.0 g I/kg of body weight, and most preferably, in the range of from about 1.0 to about 3.0 g I/kg body weight for regular X-ray visualization of the GI tract. For CT scanning the contrast agents of the present invention will be in the range of from about 1 to about 800 mg I/kg body weight, preferably in the range of from about 15 to about 250 mg I/kg body weight, and most preferably in the range of from about 35 to about 90 mg I/kg body weight.

The concentration of the iodinated polymeric beads should be in the range of from about 5% w/w to about 95% w/w of the formulation, preferably from about 10% w/w to about 60% w/w and most preferably of from about 15% w/w to about 40% w/w.

The concentration of the film forming polymeric material depends on the particular polymer used, however, it should be in the range of 0.01 to about 25% w/w or higher in combination with a divalent substance, such as calcium lactate, having a concentration range of 0.001 to 20% w/w of the cationic element. Dosage level of the polymeric material may be in the range of from about 2 to about 20 g/kg body weight or higher.

The compositions of the present invention possess very good adherence to the walls of the gastrointestinal tract by forming an essentially uniform coating thereon.

The invention, having been fully described, it will be apparent to one skilled in the art that changes and modifications can be made thereto without departing from the spirit and scope thereof.

What is claimed is:
1. A method of carrying out x-ray examination of the gastrointestinal tract of a patient, said method comprises the oral or rectal administration to the patient an x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v;

(a) of from about 0.001 to about 25% of a polymeric material capable of forming a film membrane on the gastrointestinal tract in the pH range of form about 5 to 8, said polymeric material being selected from the group consisting of:
dermatan sulfate,
hepatosulfate,
hyabromic acid,
heparin,
chitin,
polyvinylpyrrolidone,
polyvinyl alcohol and
ethylene oxide;

(b) of from about 0.1 to about 20% of a divalent cation to potentiate the binding of said flexible film membrane to said mucosal lining selected from the group consisting of $Ca^{++}$, $Mg^{++}$, $Zn^{++}$ and $Ba^{++}$; and c) of from about 5 to about 95% of an iodinated polymeric, water-insoluble beads having a particle size of from about 0.01 to about 1000μ wherein said iodinated polymeric beads comprise a polymer containing repeating units of the formula (I)

   I wherein
A is a repeating organic unit in the backbone chain of the polymer; and
X is an organic moiety containing an iodinated aromatic group and a hydrophilic group, said moiety having an iodine content within the range of from about 40 to about 80 weight percent based on the molecular weight of X, in a liquid pharmaceutically acceptable carrier comprising:
a surfactant selected from the group consisting of
cetyltrimethyl ammonium bromide,
dodecyl ammonium bromide,
sodium lauryl sulfate,
sodium heptadecyl sulfate,
alkyl benzene sulfonic acid,
sodium butylnaphthalene sulfonate,
sodium butylnaphthalene sulphosucinate,
carboxylic esters,
carboxylic amides,
ethoxylated alkylphenols,
ethoxylated aliphatic alcohols,
sorbitan esters,
polyoxyethylene alkyl ethers and
polyoxyethylene sorbitan fatty acid esters; and exposing the gastrointestinal tract containing said x-ray contrast composition to x-rays to form an x-ray image pattern corresponding to the presence of said x-ray contrast composition, and visualizing said image pattern.

* * * * *